(12) United States Patent
Bene et al.

(10) Patent No.: US 8,512,564 B2
(45) Date of Patent: Aug. 20, 2013

(54) CONTROL APPARATUS AND CONTROL METHOD FOR A BLOOD TREATMENT EQUIPMENT

(75) Inventors: Bernard Bene, Iringy (FR); Georges Vantard, Villefontaine (FR); Carl W. Reitz, Riehen (CH)

(73) Assignee: Gambro Lundia AB, Lund (SE)

( * ) Notice: Subject to any disclaimer, the term of this patent is extended or adjusted under 35 U.S.C. 154(b) by 2333 days.

(21) Appl. No.: 10/526,498

(22) PCT Filed: Sep. 4, 2003

(86) PCT No.: PCT/IB03/03745
§ 371 (c)(1),
(2), (4) Date: Sep. 29, 2005

(87) PCT Pub. No.: WO2004/022135
PCT Pub. Date: Mar. 18, 2004

(65) Prior Publication Data
US 2006/0157413 A1 Jul. 20, 2006

(30) Foreign Application Priority Data
Sep. 5, 2002 (EP) .................................. 02078806

(51) Int. Cl.
*B01D 29/00* (2006.01)
(52) U.S. Cl.
USPC ............ 210/251; 210/93; 210/418; 210/646; 210/739; 600/366
(58) Field of Classification Search
USPC ................. 210/646, 93, 739; 604/4.01, 5.01; 600/366
See application file for complete search history.

(56) References Cited

U.S. PATENT DOCUMENTS

| 4,244,787 A | 1/1981 | Klein et al. |
| 4,508,622 A | 4/1985 | Polaschegg et al. |

(Continued)

FOREIGN PATENT DOCUMENTS

| DE | 4 024 434 | 2/1992 |
| DE | 197 47 360 | 4/1999 |

(Continued)

OTHER PUBLICATIONS

Keshaviah, P. and Collins, A. Rapid High-efficiency Bicarbonate Hemodialysis. *Trans. Am. Soc. Artif. Intern. Organs*, vol. 32, 1986, pp. 17-23.

(Continued)

*Primary Examiner* — Dirk Bass
(74) *Attorney, Agent, or Firm* — Nixon & Vanderhye P.C.

(57) ABSTRACT

It is disclosed a controller for a blood treatment equipment comprising at least a treatment unit including a semipermeable membrane separating the treatment unit in a first compartment for the circulation of blood and in a second compartment for the circulation a of a treatment liquid; the controller is adapted to receive one or more entries of measured information measured during the course of a treatment procedure, calculate from said measured information a value of at least a significant parameter indicative of the progress of an extracorporeal blood treatment carried out by the equipment, wherein the controller is also adapted to compare said calculated significant parameter to at least a prescribed reference value for the same parameter, and to generate at least one output control signal responsive to said comparison for automatically controlling one or more operations performed by the equipment. The invention relates also to an equipment comprising the controller and to a control method the controller can be programmed to carry out.

39 Claims, 7 Drawing Sheets

(56) References Cited

U.S. PATENT DOCUMENTS

| | | | |
|---|---|---|---|
| 5,024,756 A * | 6/1991 | Sternby | 210/93 |
| 5,230,702 A * | 7/1993 | Lindsay et al. | 604/4.01 |
| 5,567,320 A | 10/1996 | Goux et al. | |
| 5,744,031 A | 4/1998 | Bene | |
| 6,110,384 A * | 8/2000 | Goux et al. | 210/739 |
| 6,258,027 B1 * | 7/2001 | Sternby | 600/366 |
| 6,648,845 B1 * | 11/2003 | Gotch et al. | 604/5.01 |

FOREIGN PATENT DOCUMENTS

| | | |
|---|---|---|
| EP | 0 097 366 | 1/1984 |
| EP | 0 330 892 A | 9/1989 |
| EP | 0 495 412 A1 | 7/1992 |
| EP | 0 532 433 A1 | 3/1993 |
| EP | 0 658 352 | 6/1995 |
| JP | 1-131670 | 5/1989 |
| JP | 6-14994 | 1/1994 |
| JP | 6-500946 | 1/1994 |
| WO | WO 93/00938 | 1/1993 |
| WO | WO 98 55166 A | 12/1998 |

OTHER PUBLICATIONS

Gotch, F. and Sargent, JA. *A mechanistic analysis fo the National Cooperative Dialysis Study (NCDS)*. Kidney Int'l., vol. 28, 1985, pp. 526-534.

Gotch, Frank A., "Kt/V is the Best Dialysis Dose Parameter," Karger, Blood Purif 2000, pp. 276-285.

Gunther Schonweib, "Dialyse Primer" ISBN 3-9319116-01-4, 1996, 13 pages (with English Translation (27 pages)).

OCM, "Impulse for Increased Quality of Life", Fresenius Medical Care, 2001, 6 pages (with English Translation (5 pages)).

IEC 60601-2-16, Medical Electrical Equipment—Particular Requirements for Safety of Haemodialysis, Haemodiafiltration and Haemofiltration Equipment, 1998, 24 pages.

"Hamodialysegerate", 408 H/S, Sichtbar bessere Dialyseergebnisse, Fresenius Medical Care, 2001, 8 pages.

"Hamodialysegerate", 4008 H/S, Sichtbar bessere Dialyseergebnisse, Fresenius Medical Care, 2001, 8 pages (w/ English Translation).

* cited by examiner

CONTROL APPARATUS AND CONTROL METHOD FOR A BLOOD TREATMENT EQUIPMENT

CROSS REFERENCE TO RELATED APPLICATIONS

This application is a national phase application based on PCT/IB2003/003745, filed Sep. 4, 2003, the content of which is incorporated herein by reference, and claims the priority of European Patent Application No. 02078806.3, filed Sep. 5, 2002.

FIELD OF INVENTION

This invention relates to a control apparatus and control method for a blood treatment equipment. The present invention relates also to a blood treatment equipment comprising said control apparatus.

More particularly, the invention is concerned with an apparatus, such as a programmable computer, capable of operating on a blood treatment equipment such as an hemodialysis or other blood treatment equipment; the programmable controller is adapted to receive entries of prescribed and measured information and to generate one or more output signals in response thereto. In general the output signals are employed to control a variable operation performed by the blood treatment equipment and hence automatically perform treatment procedure control methods.

BACKGROUND OF THE INVENTION

It is known in the art of hemodialysis and other blood treatment machines using measured values of certain parameters in order to control the working of the machine.

For instance, EP097366 and U.S. Pat. No. 4,508,622 both disclose a device provided with two conductivity cells 32,50 on the dialysis liquid side; one cell operates upstream the dialyzer and the other downstream the dialyzer. The two cells are able to measure conductivity of the dialysis liquid or sodium concentration. The measured data of detectors are compared and eventually used to control the composition of the dialysis solution.

In Gambro EP0330892, it is of advantage to employ measured values of a patient's conditional values to control functional aspects of hemodialysis equipments. In this fashion, the hemodialysis equipment may be controlled dependently of specific treatment requirements of a patient. In particular, this reference teaches to determine the concentration for a certain solute in patient's blood and other important parameters as actual clearance (indicated herein as K in ml/min) or dialysance values (expressed herein as D in ml/min). If for instance the system of EP0330892 is adapted for determining sodium concentration or conductivity of patient's blood, the dialysis liquid concentration can be controlled in order to bring about an equilibrium between the conductivities of blood and dialysis liquid, thereby obtaining a control adapted to the individual which should provide comfort for the patient.

It is also known from EP0532433 a blood treatment device able to detect actual sodium dialysance and then derive urea clearance by extrapolation. Such a calculated urea clearance is then compared with a desired urea clearance value and in case of need the flow rate of the dialysis pump or of the blood pump, or the treatment time are changed. In case treatment time is changed also the UF rate of the ultrafiltration pump is modified.

On the other hand during the last twenty years a specific index, the KT/V index, has been regarded as particularly indicative of the dialysis treatment. More in detail Keshaviah and Collins (Keshaviah P, Collins A: Rapid high-efficency bicarbonate hemodialysis, Trans Am Soc Artif Intern Organs 32: 17, 1986) reported in a well documented and well designed study on short dialysis, using the KT/V index as a parameter of dialysis adequacy. This index, introduced in 1985 by Gotch and Sargent (Gotch F, Sargent JA: A mechanistic analysis of the National Cooperative Dialysis Study (NCDS). Kidney Int. 28: 526, 1985) is calculated as the product of the urea clearance (K, ml/min) of the dialyser and duration of the dialysis session (T, min), divided by the distribution volume of urea (V ml). Gotch and Sargent analysed the data of the large scale National Cooperative Dialysis Study (NCDS) in the US and determined that a KT/V value of 0.9-1.0 constitutes adequate dialysis therapy. Values less than 0.8 are associated with a high probability of therapy failure. Keshaviah and Collins (Keshaviah P, Collins A: Rapid highefficiency bicarbonate hemodialysis, Trans Am Soc Artif Intern Organs 32: 17, 1986) also demonstrated that short and rapid dialysis treatment is well tolerated when acetate is replaced by bicarbonate and is not associated with increased mortality and morbidity if therapy is prescribed keeping KT/V greater than 1.

In view of the above works, the value D or K for a certain solute (Notice again that Durea=Kurea) have been employed to determine value $K*T_i$, herein indicated as dialysis dose achieved after time $T_i$.

The approach presently followed in the blood treatment machines available on the marketplace is to obtain a measure of and to provide information related to a total dialysis dosage K*T value delivered as time progresses during a hemodialysis treatment procedure. This measure and the information provided is essentially based on parameters including:
  a prescribed duration of the treatment procedure,
  the blood flow rate,
  the choice of the hemodialyser A combination of above parameters is employed to obtain a measure of the total dialysis dosage value $K*T_t$ delivered as an integral of mean measured instantaneous clearance values measured after determined time increments, the dialysance of the chosen dialyser (which is an in vitro clearance value) and the effective treatment time. The effective treatment time is the time during which diffusive (and generally also convective) transfer of blood solutes across a semi-permeable membrane of a hemodialyser takes place.

The above procedure basically enables a measure to be made of the K*T value delivered to a patient during a hemodialysis treatment procedure.

At the end of the treatment which normally lasts a prefixed total time $T_{tot}$, the machine provides the user with the value of K*Ttot and with the value K*Ttot/V.

This procedure, however, suffers from a number of drawbacks. Specifically, such factors as blood flow rate and effective treatment time, which are relevant to clearance, are prone to change or are difficult to follow during a hemodialysis treatment procedure. Furthermore, the dialysance or clearance capacity of hemodialyser products can change significantly during a hemodialysis treatment procedure time. Present day hemodialysis monitoring equipment and hemodialysis procedure methods may comprise means for assessing or measuring dialysis dosages delivered to a patient over determined time increments, but no means are available for controlling the dialysis dosage value actually delivered to the patient, on an ongoing bases during treatment, and for carrying out actions on the dialysis machine working parameters as a function of the detected dialysis dosage delivered to the patient.

It is an overall objective of the present invention to secure an ongoing control over the actual total dialysis dosage delivered to a patient.

It is another object of the invention to control some parameters of a blood treatment machine as a function of the values of the dialysis dose measured in the course of the treatment.

Furthermore, it an object of the invention to provide a control apparatus and a blood treatment equipment able to coordinate achievement of the prescribed dialysis dose with substantially contemporaneous achievement of other prescription(s).

A further object is to provide a system for synchronizing achievement of a prescribed dialysis dose, of a prescribed weight loss and of a further prescribed prescription, such as concentration of a certain substance in patient's blood.

Another object of the invention is to offer a system, which is adapted to reduce, if possible, the treatment time while achieving the requested prescribed results at the end of the treatment.

Moreover it is an object of the invention to provide a controller and an equipment using said controller able to display updated values for a number of parameters, on ongoing basis at regular intervals during treatment.

SUMMARY OF THE INVENTION

The above and other objects are reached by a controller, by a control method and by an equipment according to one or more of the appended claims.

The controller according to the invention is adapted to receive one or more entries of measured information measured during the course of a treatment procedure, calculate from said measured information at least a significant parameter indicative of the progress of an extracorporeal blood treatment carried out by the equipment, compare said calculated significant parameter to at least a prescribed reference value for the same parameter, and to generate at least one output control signal responsive to said comparison for automatically controlling one or more operations performed by the equipment. The significant parameter can be one chosen in the group comprising:

the actual dialysance $D_{Ti}$ or clearance $K_{Ti}$ of a blood treatment unit associated with the equipment for a specific solute after a time $T_i$ elapsed from the beginning of the treatment;

the concentration of a substance in the blood of a patient undergoing a treatment or the patient's plasmatic conductivity $Cp_{Ti}$ achieved at the elapsed time $T_i$;

the dialysis dose $K^*T_{Ti}$ achieved at the elapsed time $T_i$;

the weight loss $WL_{Ti}$ achieved at the elapsed time $T_i$;

a parameter proportional or known function of one or more of the above parameters.

The controller is adapted for receiving measured information from a conductivity sensor operating downstream the treatment unit or from a concentration sensor, again operating downstream the treatment unit, calculates at regular time intervals the achieved value of dialysis dosage and regulates the removal rate from the second compartment in order to have achievement, at the end of the treatment, of both the total prescribed dialysis dosage value $KT_p$ and the prescribed total weight loss $WL_p$.

The removal rate can be controlled by changing the speed of an ultrafiltration pump or if the equipment does not include a pump devoted to ultrafiltration only, by changing the speed of a pump associated to the waste line at the output of the second compartment.

The controller can be programmed for estimating at regular time intervals the remaining treatment procedure time $T_{tr}$ or the total treatment time $T_{tot}$ necessary for achieving the prescriptions.

The controller can also be programmed for keeping said rate of fluid removal $UF_{Ti}$ at time $T_i$ substantially equal to the product of a factor R, determined by the ratio between $WL_p$ and $KT_p$, by the instantaneous clearance $K_{Ti}$ or instantaneous dialysance value $D_{Ti}$ measured at treatment time $T_i$. In this case the controller synchronizes two prescriptions and ends the treatment at the prescribed values are reached with no need of calculating the remaining treatment time or the treatment time at each interval.

Safety measures may be provided to avoid that the treatment time or the fluid removal from the second compartment fall outside prescribed ranges.

Note that the prescribed reference value may comprise a patient blood conductivity or concentration target $Cp_{end}$: in this case the controller is programmed for controlling the conductivity or concentration of the treatment liquid entering the second compartment as a function of a blood conductivity or concentration target $Cp_{end}$ in order to have blood conductivity or concentration for a substance reaching said conductivity or concentration target $Cp_{end}$ on or before said estimated total treatment time $T_{tot}$.

Alternatively the controller is programmed for controlling the conductivity or concentration of the treatment liquid entering the second compartment for reaching said conductivity or concentration target $Cp_{end}$ when another prescription is reached (for instance total prescribed weight loss or total prescribed dialysis dose), with no need of calculation of a remaining treatment time.

According to a further aspect, the controller is associated with a display screen adapted to display at the time intervals $T_i$ one or more of the values of the group comprising:

remaining time $T_{tr}$.

total treatment time $T_{tot}$, clearance of dialysance measurements at the elapsed time $T_i$, achieved dialysis dosage $KT_{Ti}$ after $T_i$ time, achieved weight loss $WL_{Ti}$ after $T_i$ time, achieved patient's conductivity after $T_i$ time, prescribed value for more of the significant parameters, a value proportional to one or more of the above values.

The invention also relates to a control method.

The invention furthermore concerns program storage means including a program for a programmable controller, the program when run by the controller programming the controller to carry out the steps disclosed in the claims.

An important difference between the invention as described above and approaches followed in the past is that the treatment procedure time involved in the present invention need not be a prescribed time but may be a time which is dependent on achievement of a prescribed value. Thus, in accordance with the invention, the treatment time may be controlled by measured information which can be related to a measure of an effective clearance value of a substance (usually urea is the reference substance) measured after a determined time increment during a hemodialysis treatment procedure.

Notice that clearance values are influenced by ultrafiltration, which leads to convective transfer of solutes in blood plasma across a semi-permeable membrane of a hemodialyser product into dialysis fluid. In practically all hemodialysis treatment procedures, ultrafiltration to achieve loss of excess fluid in the patient is required. The controller is therefore adapted to include or account for the convective clearance, which follows from ultrafiltration. Most preferably, therefore, the controller should be adapted to provide output information related to both the diffusive and convective clearance values or conveniently an integrated measure of these two values.

DESCRIPTION OF THE DRAWINGS

The invention will be described with reference to the accompanying exemplary drawing tables, wherein.

DETAILED DESCRIPTION

Figure 1:
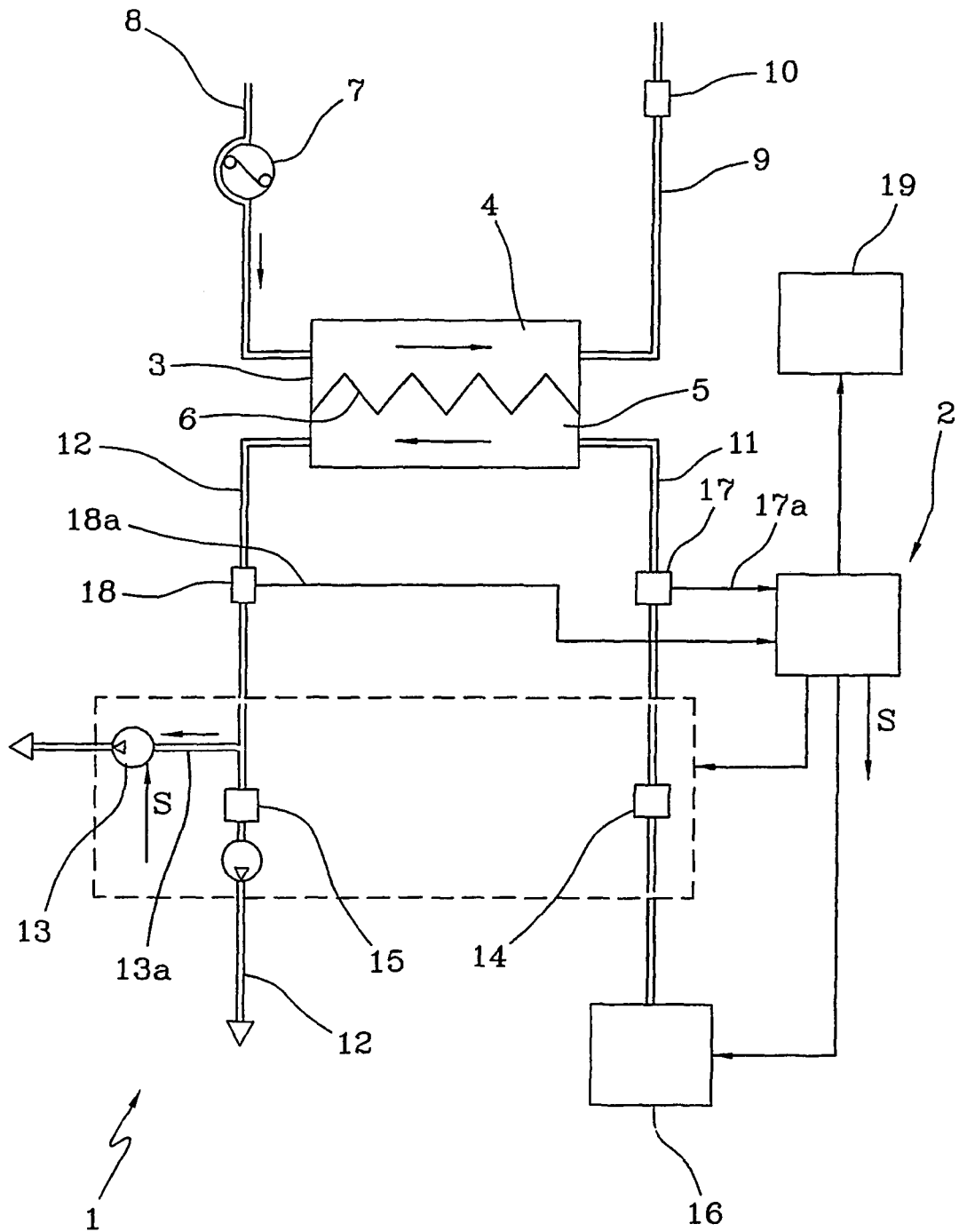
FIG. 1 is a schematic drawing of hemodialysis equipment associated with a controller according to the invention.

Specific embodiments of a controller and of a blood treatment equipment, associated with or comprising a controller according to the invention, are described below. For the purpose of this description reference is made to a specific blood treatment equipment, namely a dialysis equipment. However the invention is not limited to such equipment and can be used in conjunction to other kinds of blood treatment machines. With reference to specification, including the accompanying schematic drawings and the claims, the symbols below will have the meanings identified as follows:

$T_{tot}$=total treatment time
$T_i$=elapsed treatment time, i.e. effective treatment time elapsed from the beginning of the treatment session
$T_{tr}$=remaining treatment time
$T_{max}$=maximum treatment time
$T_{min}$=minimum treatment time
$D_a$=average dialysance
$D_{Ti}$=actual dialysance at time $T_i$
$K_a$=average clearance
$K_{Ti}$=actual clearance at time $T_i$
$K_{Ti}$=dialysis dosage value
$KT_p$=prescribed dialysis dosage value
$KT_{Ti}$=integrated dialysis dosage value at time $T_i$
WL=weight loss
$WL_p$=prescribed weight loss
$WL_{Ti}$=weight loss at time $T_i$
UF=fluid removal rate from the second compartment of the treatment unit
$UF_{Ti}$=fluid removal rate from the second compartment of the treatment unit at time $T_i$ Referring now to FIG. 1 schematic drawing, reference numeral I refers generally to a blood treatment equipment, such as for instance hemodialysis equipment, comprising or associated with a controller 2, for instance a programmable controller. The equipment as shown is connected to a blood treatment unit 3, such as a hemodialyser, comprising a first or blood compartment 4 and a second or dialysate compartment 5 divided by a semi-permeable membrane 6. A blood pump 7 is provided upstream of the hemodialyzer for pumping blood from a patient along blood arterial line 8 into the blood compartment and out from the blood compartment along blood venous line 9 to drip chamber 10 and back to the patient (not shown). Of course the position and number of blood pumps and the specific treatment unit indicated in the embodiment of FIG. 1 are for exemplifying purpose only and are not intended to limit the scope of the invention.

Dialysate, coming for instance from a dialysate preparation section 16, is conveyed into the dialysate compartment 5 along dialysate inlet line 11 and out from the dialysate compartment along dialysate outlet line 12 in a direction countercurrent to blood flow in the hemodialyzer. A fluid balancing system is responsible of controlling the amount of fluid entering the second compartment and the amount of fluid exiting the second compartment so as to create a desired weight loss rate during treatment. For instance, the balancing system may be associated to a variable speed ultrafiltration pump 13 operating on an ultrafiltration line 13a branching off line 12 and provided for pumping ultrafiltrate from blood compartment across the semi-permeable membrane into the dialysate chamber and out from the dialysate outlet line 12. The balancing system can comprise conventional means, e.g. flow meters 14, 15 located upstream and downstream of the hemodialyzer product 3 in the way shown in FIG. 1. The flow meters are connected to controller 2 so that the controller is able to act at least on the ultrafiltration pump and on the waste pump 12a to keep the flow rate of the fresh dialysis liquid measured by flow meter 14 equal to the used liquid flow rate measured by flow meter 15. As the ultrafiltration pump 13 branching off conduit 12 operates upstream the flowmeter 15, such pump 13 flow rate defines the weight loss rate. Other balancing systems may comprise controlling volumes and/or weights of dialysate delivered to and withdrawn from the dialysate compartment. An infusion line may also be provided with (not shown in the appended drawing tables) for injecting replacement fluid in the arterial and/or in the venous line 8, 9. The infusion line flow rate can be obtained by variable speed pumps, which can be controlled by flow meters or volumeters or weight meters associated to the infusion line. In case of use of one or more infusion lines, also the flow rate of any infusion liquid needs to be accurately controlled during treatment, in order to control the overall balance of liquid. In this respect, notice that flow rate sensors or volumetric sensors are generally used when the dialysis or the infusion line are generated online or come from a continuous source of liquid, while weight sensors are typical of embodiments wherein the liquids are withdrawn from or conveyed to containers. For instance in case of a hemodialysis circuit using a fresh dialysate bag and a waste container, it is known to use one or two separate scales associated to the containers in order to provide a controller with an information concerning the overall weight difference between the fluid entering the second compartment of the dialyzer and the fluid exiting the second compartment.

It is clear for those skilled in the art that the present invention can be used in any kind of blood treatment machine, independently from the specific balancing system.

Going now back to the detailed description of the embodiment of FIG. 1, the equipment 10 can be adapted to perform different treatments such as:

conventional hemodialysis, HD, where no infusion is present and dialysis liquid circulates in the second compartment of the dialyzer (FIG. 1);

hemofiltration, HF, where no dialysis liquid is present while solutes and plasma water are pumped through line 12 and substitution fluid (not shown) is infused in the extracorporeal circuit or directly into the patient;

hemodiafiltration, HDF, which is a combination of HD and HF;

other blood treatments in case the treatment unit is correspondingly modified.

After the above description of the general structure of equipment 1, here below a more detailed analysis of the controller 2 will be provided.

Controller 2 comprises at least a programmable microprocessor with associated memories and interfaces suitable to communicate with the components of equipment 1. Of course the present invention controller could also comprise an analogical type calculator, though this embodiment is not felt to be the most appropriate in term of costs and flexibility.

The controller 2 is adapted to receive one or more entries of measured information measured during the course of a treatment procedure. In the embodiments shown the measured information comprises the conductivity of the dialysis liquid or the concentration of the dialysis liquid for at least a substance, measured downstream the dialyzer 3, i.e. on line 12. As shown in FIG. 1 the controller is connected with measuring means 18 for measuring the conductivity of the treatment liquid downstream the treatment unit. Alternatively the controller may be connected to means for measuring the concentration of a substance in the treatment liquid downstream the treatment unit. Since the measured information may also comprise the conductivity of the dialysis liquid or the concentration of the dialysis liquid for at least a substance, measured upstream the dialyzer 3, i.e. on line 11, the equipment 1 of FIG. 1 also includes measuring means 17 for measuring at least one of the conductivity of the treatment liquid upstream the treatment unit, or of the concentration of a substance in the treatment liquid upstream the treatment unit. The measurements carried out by the measuring means 17 operating upstream the treatment unit could be substituted by set or known values of conductivity or concentration. Notice that if the measured information is the urea concentration, it is not even necessary to carry out a measurement upstream as urea is absent from fresh dialysis liquid.

In case the measuring means are devoted to measure conductivity, then each measuring means 17, 18 comprises at least a conductivity cell. If the measuring means are devoted to measure an ion's concentration then said means comprises an ion selective sensor or a urea sensor (notice again that in case of measure of a quantity absent in fresh dialysis liquid—as urea—then there is no need to use a sensor on line 11).

The controller I is then programmed to calculate from the measured information (for instance from the value of the conductivity upstream and downstream the treatment unit) a value of at least a significant parameter indicative of the progress of an extracorporeal blood treatment carried out by the equipment.

According to the invention the significant parameter is one chosen in the group comprising:

the actual dialysance $D_{Ti}$ or clearance $K_{Ti}$ of a blood treatment unit associated with the equipment for a specific solute after a time $T_i$ elapsed from the beginning of the treatment;

the concentration of a substance in the blood of a patient undergoing a treatment or the patient's plasmatic conductivity $Cp_{Ti}$ achieved at the elapsed time $T_i$;

the dialysis dose $K*T_{Ti}$ achieved at the elapsed time $T_i$;

the weight loss $WL_{Ti}$ achieved at the elapsed time $T_i$;

a parameter proportional or known function of one or more of the above parameters.

Finally, the controller is adapted to compare said calculated significant parameter to at least a prescribed reference value for the same parameter, and to generate at least one output control signal responsive to said comparison for automatically controlling one or more operations performed by the equipment.

For instance, the controller 1 after having compared the calculated value of one or more significant parameters with the corresponding reference value for the same parameter may generate the output control signal responsive to said comparison for automatically controlling a fluid removal rate from said second compartment.

Note that the measurement of the measured information, the calculation of the significant parameter(s), and the comparison with the respective reference value are done during the treatment (or at least during an effective portion of the treatment) on an ongoing basis, at regular time intervals, as it will be described in detail here below with reference to the embodiments shown in the drawing tables.

The way that is felt to be the easiest for implementing the invention provides that the time intervals are indeed constant and prefixed, for instance equal to 15 minutes each. However, the invention can be implemented also using regular but not constant time intervals: i.e. time intervals following a specified rule or rules, which the controller should know or made aware of.

Figure 2:
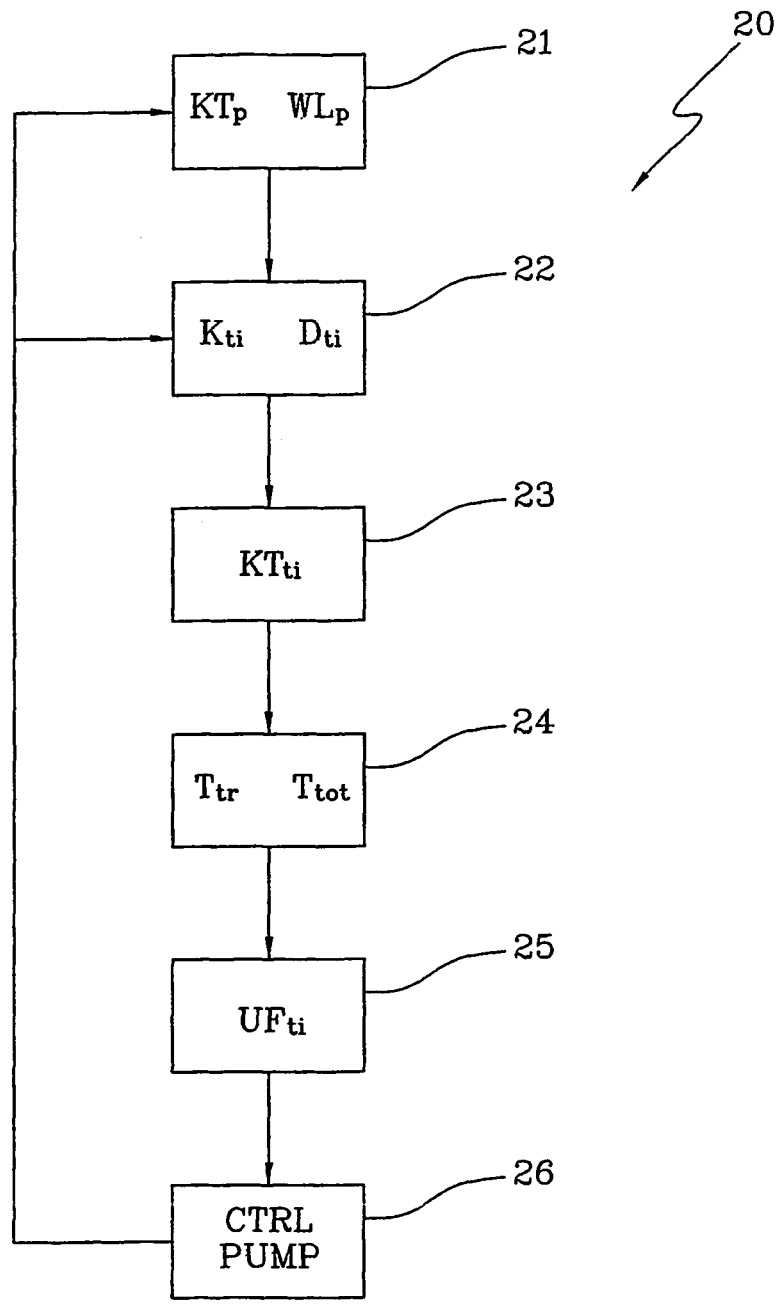
FIG. 2 is a flow diagram showing the working principle of a controller according to a first embodiment of the invention.

In a first embodiment, the controller 2 is programmed to carry out the steps shown in FIG. 2.

After having started the treatment, the controller waits for a prefixed time, for instance 10 or 15 minutes, and then carries for the first time the loop shown in FIG. 2, loop cycle 20, which is then repeated at each successive time interval.

More in detail, according to this embodiment, the controller is programmed for determining the estimated remaining treatment procedure time $T_{tr}$ and/or the estimated total treatment time $T_{Tot}$ as a function of a calculated value of a significant parameter at time $T_i$. In other words the controller is able to modify the duration of the treatment if certain actual values of parameters deemed to be significant change during treatment.

In particular, the controller according to the first embodiment receives (as a first step 21 of the loop cycle 20) the prescribed values for the dialysis dosage $KT_p$ and for the total weight loss $WL_p$ to be achieved at the end of the treatment.

Then, as second step 22, determines the instantaneous clearance $K_{Ti}$ or dialysance value $D_{Ti}$ corresponding to the conductivity or concentration measurements at treatment time $T_i$. Then, the controller calculates the effective dialysis dosage $KT_{Ti}$ achieved at time $T_i$ (step 23). Once calculated $KT_{Ti}$, the controller proceeds with step 24 for estimating the remaining treatment procedure time $T_{tr}$ as a function of said total dialysis dosage value $KT_p$, of the effective total dialysis dosage $K_{Ti}$ achieved by time $T_i$, and of the instantaneous clearance $K_{Ti}$ or dialysance value $D_{Ti}$ measured at treatment time $T_i$. As an alternative or in conjunction with the determination of the estimated remaining treatment time, the controller 2 is programmed for determining the estimated value of the total treatment time $T_{tot}$.

The estimated value of the total treatment time can be calculated for instance as a function of said total dialysis dosage value $KT_p$, of the effective total dialysis dosage $KT_i$ achieved by time $T_i$, and of the elapsed treatment time $T_i$.

Alternatively said controller can calculate the estimated total treatment time $T_{tot}$ as sum of the elapsed treatment time $T_i$ and of the estimated value of the remaining treatment procedure time $T_{tr}$.

Once the estimated remaining treatment time or the estimated total treatment time are know at the instant $T_i$, the controller proceeds with step 25 determining an actual measured total weight loss $WL_{Ti}$ achieved by time $T_i$, and setting the fluid removal rate UF from said second compartment for achieving the prescribed total weight loss $WL_p$, substantially at the same time as the prescribed total dialysis dosage value $KT_p$ is achieved.

Notice that the control on the fluid rate removal can also be done in such a way as to achieve the prescribed total weight loss some minutes before the estimated total treatment time, which as explained derives from the calculation of the actual dialysis dosage achieved at time $T_i$.

Once corrected, if necessary (there might be the case where the flow rate extracted from the second compartment is already well tuned), the loop ends and the controller repeats the loop starting from step 21 or from step 22 at the successive time interval, i.e. after a time which can be prefixed or calculated by the controller. In the case of FIG. 2 the time interval is equal to 15 minutes.

Going in further detail, notice that the controller, which is programmed for controlling, on an ongoing basis, the fluid removal rate as a function of the estimated remaining treatment procedure time $T_{tr}$ or of estimated total treatment time $T_{tot}$, sets the fluid removal rate $UF_{Ti}$ at time $T_i$ equal to the prescribed total weight loss $WL_p$ less the measured weight loss $WL_{Ti}$ at time $T_i$, divided by the estimated remaining treatment time $T_{tr}$, according to the formula:

$$UF_{Ti} = \frac{WL_p - WL_{Ti}}{T_{tr}}$$

Alternatively, the controller can be programmed for setting of the fluid removal rate $UF_{Ti}$ at time $T_i$ equal to the prescribed total weight loss $WL_p$ less the measured weight loss $WL_{Ti}$ at time $T_i$, divided by a difference between the estimated total treatment time $T_{tot}$ and the elapsed treatment time $T_i$ according to the formula:

$$UF_{Ti} = \frac{WL_p - WL_{Ti}}{T_{tot} - T_i}$$

As explained, the controller is programmed for recalculating and updating at regular time intervals during treatment the estimated total treatment time $T_{tot}$ and/or the estimated remaining treatment time $T_{tr}$, on the basis of the value of instantaneous clearance $K_{Ti}$ or dialysance $D_{Ti}$ measured at the time $T_i$. As an alternative for determining the estimated total treatment time $T_{tot}$ and/or the estimated remaining treatment time $T_{tr}$, at instant Ti, the controller could be programmed for using recent values of clearance $K_{Ti-k}$ or dialysance $D_{Ti-k}$ (i.e. values determined at one or more time intervals before $T_i$).

In order to calculate dialysance and or clearance values during treatment any known method could be suitable. A know method provides that the instantaneous clearance value $K_{Ti}$ or instantaneous dialysance value $D_{Ti}$ is determined at treatment time $T_i$, by means of the following sub-steps:
  sending at least a first liquid through the second compartment of the treatment unit,
  sending at least a second liquid through the second compartment of the treatment unit, the second liquid having conductivity or concentration for at least a solute different from that of the first liquid
  measuring the conductivity or concentration values of said substance in the treatment liquid downstream the treatment unit at least for both said first and for said second liquid,
  calculating the instantaneous clearance $K_{Ti}$ or instantaneous dialysance value $D_{Ti}$ at least as a function of said measured conductivity or concentration values.

Further details of the above method and variants thereof are described in detail in the following publications, which are incorporated herein by reference:
EP patent n. 0547025
EP patent n. 0658352
EP patent n. 0920887

Each of the above references describes an alternative way for in vivo determination of the actual dialysance, blood sodium concentration and dialysis dose. Note that any method able to determine one or more of the above significant parameters can be used for the purpose of the present invention. Referring by way of non-limiting example to a first known method for determining the concentration of a substance in blood and/or the actual dialysance for said substance (described in detail in EP 0547025B1), at least two liquids differing for their respective concentration of said specific substance are sequentially circulated through the dialysate compartment 5. The first liquid can be the dialysis liquid at its normal prescribed value of concentration for the substance and the second liquid can be obtained by introducing a step or a change in the concentration of said substance at the dialyzer inlet. The step or the change has to be in someway known or measurable. Then the conductivity or concentration of the substance are measured for the first ad second liquid both upstream and downstream of the dialyzer. Note that the upstream measurements can be substituted by set reference values. Notice in this respect that if the substance is a ionic substance, then the concentration of the substance influences the conductivity of the dialysis liquid; in particular considering that conductivity is largely influenced by the concentration of sodium ions, than measure/calculation of conductivity values gives an indication of sodium concentration in blood and in the dialysis liquid. As conductivity sensors are much more convenient and easy to use than ion selective sensors for directly detecting the concentration of an electrolyte in a liquid flow, conductivity measurements are preferably used. Then by applying the following formula cited in EP 0547025B1 for the two dialysis liquids it is possible to determine the unknowns D and $Cb_{in}$ (no ultrafiltration and neglecting the so-called Donnan effect):

$$Cd_{out} = Cd_{in} + \frac{DTt}{Qd}(Cb_{in} - Cd_{in})$$

Wherein:
$Cd_{out}$ is the conductivity or concentration of sodium in used dialysis liquid
$Cd_{in}$ is the conductivity or concentration of sodium in fresh dialysis liquid
$Cb_{in}$ is the concentration of sodium in untreated blood
Qd is the dialysis liquid flow
$D_{Tt}$ is the dialysance of the membrane for the solute sodium at time $T_t$ (or urea clearance: notice that the size of the urea molecule being the same as the size of the sodium molecule, the capacity for these two molecules to pass through the same predetermined membrane is consequently the same. Therefore we can establish for a same membrane, the following equation: $D_{sodium}=K_{urea}$ so detection of sodium dialysance gives clearance).

Referring to the embodiment of FIG. 1, conductivity or sensors 17 and 18 are provided which are respectively located for measuring the conductivity of dialysate flowing to dialysate compartment 5 along dialysate inlet line 11. In detail, conductivity sensor 17 provides upstream dialysate conductivity measures $C_{1in}$, $C_{2in}$ relating to the conductivity of the first and second liquid upstream the dialyzer, while conductivity sensor 18 measures the conductivities $C_{1out}$, $C_{2out}$ of the first and second dialysis liquid flowing from dialysate compartment 5 along dialysate outlet line 12. The measures of conductivity (as intermittently influenced by intermittently introducing small boluses of higher or lower concentration dialysate solutions into the dialysate inlet line) are employed to determine with the above formula instantaneous sodium dialysance values (and therefore instantaneous urea clearance values $K_{Ti}$) at any point in time $T_i$ during a hemodialysis treatment procedure or after determined time increments so that a dialysis dosage $K\ T_{Ti}$, delivered at time $T_i$, may be determined. The above equation can be written for the two dialysis liquids circulated through the dialyzer so that the two unknowns $D_{Ti}$ and $Cbin_i$ can be determined. Referring again to the drawings, the periodically measured conductivity values $Cd_{1in}$, $Cd_{2in}$ and $Cd_{1out}$, $Cd_{2out}$ (1 and 2 referring to the first and second liquid respectively) are entered into the controller via lines 17a and 18a.

As mentioned the total dialysis dosage delivered up to a certain time interval is calculated and updated at each interval as function of $K_{Ti}$ or $D_{ti}$ values determined with any suitable method. In detail notice that the controller can be programmed to determine the effective total dialysis dosage $KT_{Ti}$ value, which has been delivered at the determined effective treatment time $T_i$, as an integration over time of effective instantaneous clearance $K_{Ti}$ or instantaneous dialysance $D_{Ti}$ values determined at the various regular time intervals $T_i$. Alternatively, the effective total dialysis dosage $KT_i$ value, which has been delivered at the effective treatment time $T_i$, could be calculated as the product of the treatment time $T_i$ by a mean value of effective instantaneous clearance $K_{Ti}$ or of instantaneous dialysance $D_{Ti}$ values determined at the various regular time intervals $T_i$. Of course other suitable methods could be devised.

Figure 3:
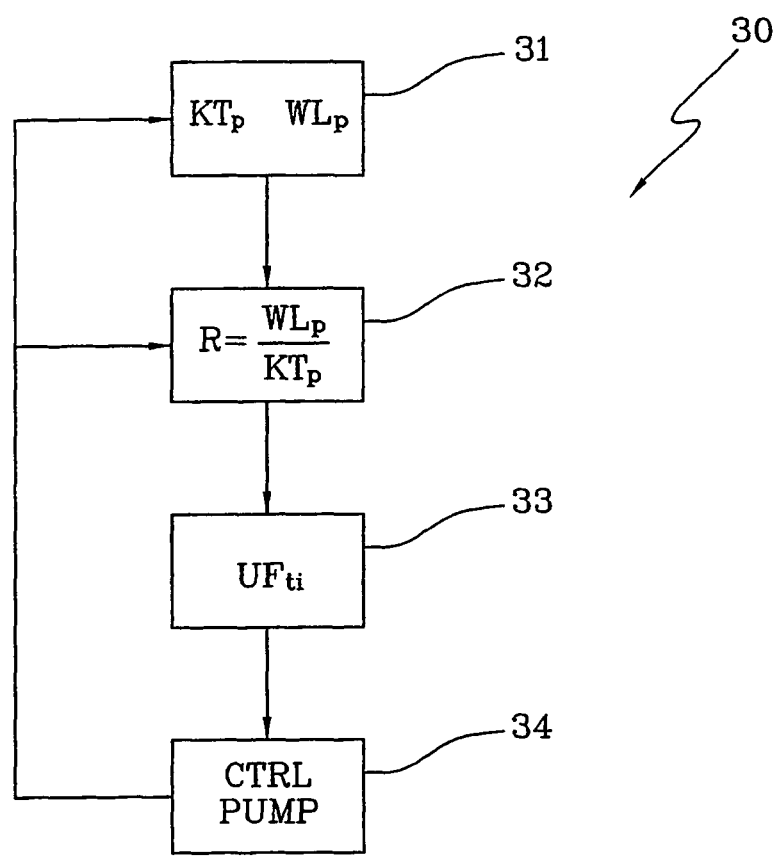
FIG. 3 is a flow diagram showing the working principle of a controller according to a second embodiment of the invention.

FIG. 3 shows the steps, which a second embodiment of the controller 2 is programmed to carry out.

After having started the treatment, the controller waits for a prefixed time, for instance 10 or 15 minutes, and then carries out for the first time the loop cycle 30 shown in FIG. 3; loop cycle 30 is then repeated at each successive time interval.

More in detail, according to this embodiment, the controller is not programmed for determining the estimated remaining treatment procedure time $T_{tr}$ and/or the estimated total treatment time $T_{tot}$, and as a matter of fact could be unaware of the actual duration of the treatment. The aim of the controller according to this second embodiment is to receive the prescribed parameters, i.e. the total clearance dosage value $KT_p$ to be achieved at the end of the treatment (step 31), and a prescribed total weight loss $WL_p$ to be achieved at the end of the treatment (step 31), and to synchronize achievement of both said parameters.

In detail the controller is programmed for determining a prescribed rate R by dividing said total weight loss $WL_p$ to be achieved at the end of the treatment by said total dialysis dose value $KT_p$ to be achieved at the end of the treatment, as shown in step 32.

Then, in steps 33 and 34, the controller controls the rate of fluid removal from the second compartment of the blood treatment, said controlling comprising keeping said rate of fluid removal $UF_{Ti}$ at time $T_i$ substantially equal to the product of said prescribed rate R by the instantaneous clearance $K_{Ti}$ or instantaneous dialysance value $D_{Ti}$ measured at treatment time $T_i$.

The loop is then concluded and the controller, as for the embodiment of FIG. 2, waits a time interval before stating again loop 30 from the step 31 or directly from step 32, if no new prescribed values shall be considered.

Notice that the instantaneous clearance $K_{Ti}$ or instantaneous dialysance value $D_{Ti}$ measured at treatment time $T_i$ can be determined as for the embodiment of FIG. 2.

Figure 4:
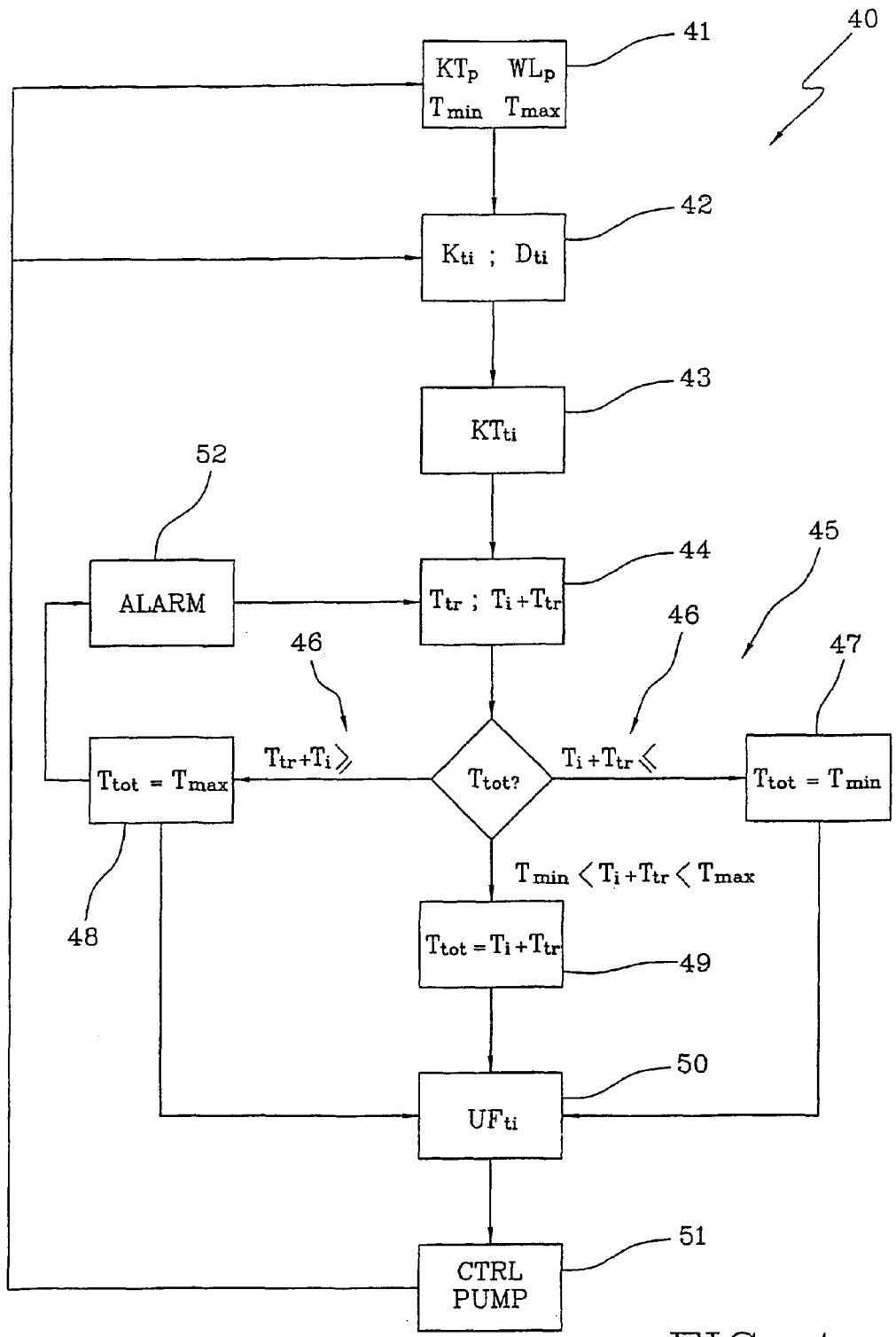
FIG. 4 is a flow diagram showing the working principle of a controller according to a third embodiment of the invention.

In FIG. 4 a further embodiment of the program steps to be followed by a controller 2 according to the present invention is shown.

The philosophy of the control loop 40 of FIG. 4 is similar to the one of FIG. 20 with some further features added.

After having started the treatment, the controller waits for a prefixed time, for instance 10 or 15 minutes, and then carries out for the first time the loop shown in FIG. 4, loop cycle 40, which is then repeated at each successive time interval.

More in detail, according to this embodiment, the controller is programmed for determining the estimated remaining treatment procedure time $T_{tr}$ and/or the estimated total treatment time $T_{Tot}$ as a function of a calculated value of a significant parameter at time $T_i$. In other words the controller is able to modify the duration of the treatment if certain actual values of parameters deemed to be significant change during treatment.

In particular, the controller according to the first embodiment receives (as a first step 41 of the loop cycle 40) the prescribed values for the dialysis dosage $KT_p$ and for the total weight loss $WL_p$ to be achieved at the end of the treatment, as well as prescribed values for a minimum acceptable treatment time $T_{min}$ and for a maximum acceptable treatment time $T_{max}$.

Then, as second step 42, determines the instantaneous clearance $K_{Ti}$ or dialysance value $D_{Ti}$ corresponding to the conductivity or concentration measurements at treatment time $T_i$. Then, the controller calculates the effective dialysis dosage $K_{Ti}$ achieved at time $T_i$ (step 43). Once calculated $KT_{Ti}$, the controller proceeds with step 44 for estimating the remaining treatment procedure time $T_{tr}$ as a function of said total dialysis dosage value $KT_p$, of the effective total dialysis dosage $KT_{Ti}$ achieved by time $T_i$, and of the instantaneous clearance $K_{Ti}$ or dialysance value $D_{Ti}$ measured at treatment time $T_i$. As an alternative or in conjunction with the determination of the estimated remaining treatment time, the controller 2 is programmed for determining the estimated value of the total treatment time $T_{tot}$.

The estimated value of the total treatment time can be calculated for instance as a function of said total dialysis dosage value $KT_p$, of the effective total dialysis dosage $KT_i$ achieved by time $T_i$, and of the elapsed treatment time $T_i$.

Alternatively said controller can calculate the estimated total treatment time $T_{tot}$ as sum of the elapsed treatment time $T_i$ and of the estimated value of the remaining treatment procedure time $T_{tr}$.

The controller is then programmed to carry out a sequence of operations globally indicated with 45 in FIG. 4 and aiming to check whether or not the estimated values of $T_{tr}$ or of $T_{tot}$ are within the prescribed ranges.

In detail, said controller, at each time interval, is programmed for executing the following sub-steps of step 45:

sub-step 46: comparing the sum $T_i+T_{tr}$ with a minimum treatment time $T_{min}$ and with a maximum treatment time $T_{max}$ sub-step 47: setting a total treatment time $T_{tot}$ equal to the minimum treatment time $T_{min}$, if said sum is less then the minimum treatment time $T_{min}$;

sub-step 48: setting a total treatment time $T_{tot}$ equal to the maximum treatment time $T_{max}$, if said sum is more then the minimum treatment time $T_{max}$;

sub-step 49: setting a total treatment time $T_{tot}$ equal to said sum if the sum is neither less then the minimum treatment time $T_{min}$ nor more then the minimum treatment time $T_{max}$ Once the total treatment time is known at the instant $T_i$, the controller proceeds with step 45 determining an actual measured total weight loss $WL_{Ti}$, achieved by time $T_i$, and setting the fluid removal rate UF from said second compartment for achieving the prescribed total weight loss $WL_p$, substantially at the end of said treatment time $T_{tot}$. Notice that if the controller determines in step 46 that the remaining treatment time is such that a superior time limit for the whole treatment $T_{max}$ cannot be fulfilled, the controller can activate an alarm procedure 52 and ask for intervention of an operator.

If vice versa the remaining treatment time is acceptable, notice that the control on the fluid rate removal can also be done in such a way as to achieve the prescribed total weight loss some minutes before the estimated total treatment time, which as explained derives from the calculation of the actual dialysis dosage achieved at time $T_i$.

Once corrected the fluid removal rate from the second compartment, if necessary (there might be the case where the flow rate extracted from the second compartment is already tuned), the loop ends and the controller repeats the loop starting from step 41 or from step 42 at the successive time interval, i.e. after a time which can be prefixed or calculated by the controller In the case of FIG. 4 the time interval is equal to 15 minutes.

Going in further detail, notice that the controller, which is programmed for controlling, on an ongoing basis, the fluid removal rate as a function of the estimated remaining treatment procedure time $T_{tr}$ or of estimated total treatment time $T_{tot}$, sets the fluid removal rate $UF_{Ti}$ at time $T_i$ equal to the prescribed total weight loss $WL_p$ less the measured weight loss $WL_{Ti}$ at time $T_i$, divided by the estimated remaining treatment time $T_{tr}$, according to the formula:

$$UF_{Ti} = \frac{WL_p - WL_{Ti}}{T_{tr}}$$

Alternatively, the controller can be programmed for setting of the fluid removal rate $UF_{Ti}$ at time $T_i$ equal to the prescribed total weight loss $WL_p$ less the measured weight loss $WL_{Ti}$ at time $T_i$, divided by a difference between the estimated total treatment time $T_{tot}$ and the elapsed treatment time $T_t$ according to the formula:

$$UF_{Ti} = \frac{WL_p - WL_{Ti}}{T_{tot} - T_i}$$

As explained, the controller is programmed for recalculating and updating at regular time intervals during treatment the estimated total treatment time $T_{tot}$ and/or the estimated remaining treatment time $T_{tr}$, on the basis of the value of instantaneous clearance $K_{Ti}$ or dialysance $D_{Ti}$ measured at the time Ti. As an alternative for determining the estimated total treatment time $T_{tot}$ and/or the estimated remaining treatment time $T_{tr}$, at instant Ti, the controller could be programmed for using recent values of clearance $K_{Ti-k}$ or dialysance $D_{Ti-k}$ (i.e. values determined at one or more time intervals before $T_i$).

In order to calculate dialysance and or clearance values during treatment any known method could be suitable as for the embodiment of FIG. 2.

As mentioned the total dialysis dosage delivered up to a certain time interval is calculated and updated at each interval as a function of KTi or Dti values. In detail notice that the controller can be programmed to determine the effective total dialysis dosage $KT_{Ti}$ value, which has been delivered at the determined effective treatment time $T_i$, as an integration over time of effective instantaneous clearance $K_{Ti}$ or instantaneous dialysance $D_{Ti}$ values determined at the various regular time intervals $T_i$. Alternatively, the effective total dialysis dosage $KT_i$ value, which has been delivered at the effective treatment time $T_i$, could be calculated as the product of the treatment time $T_i$ by a mean value of effective instantaneous clearance $K_{Ti}$ or of instantaneous dialysance $D_{Ti}$ values determined at the various regular time intervals $T_i$. Of course other suitable methods could be devised.

Figure 5:
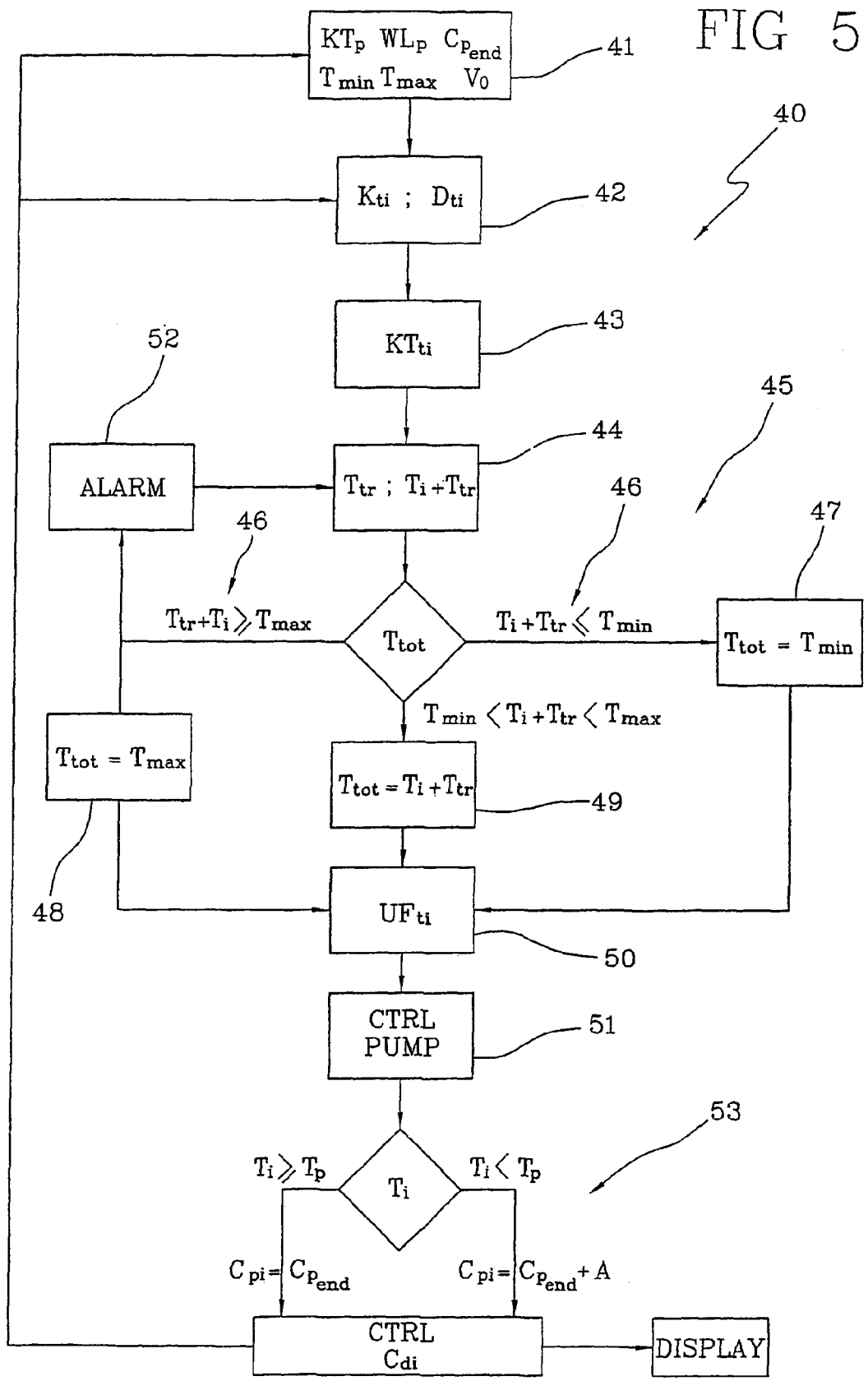
FIG. 5 is a flow diagram showing the working principle of a controller according to a fourth embodiment of the invention.

In FIG. 5 a variant program loop is shown, which the controller 2 can be programmed to execute. Control loop 40 of FIG. 5 is almost identical to the loop 40 of FIG. 4 and will not be described again in detail: the same reference numerals being used to identify corresponding features or steps.

As in the embodiment of FIG. 4, after having started the treatment, the controller waits for a prefixed time, for instance 10 or 15 minutes, and then carries out for the first time the loop shown in FIG. 5, which is then repeated at each successive time interval.

More in detail, according to this embodiment, the controller is programmed for determining the estimated remaining treatment procedure time $T_{tr}$ and/or the estimated total treatment time $T_{Tot}$ as a function of a calculated value of a significant parameter at time $T_i$. In other words the controller is able to modify the duration of the treatment if certain actual values of parameters deemed to be significant change during treatment.

Differently from the embodiment of FIG. 4, the controller programmed to execute the steps of FIG. 5 receives (as a first step 41 of the loop cycle 40):

the prescribed values for the dialysis dosage $KT_p$ and for the total weight loss $WL_p$ to be achieved at the end of the treatment, prescribed values for a minimum acceptable treatment time $T_{min}$ and for a maximum acceptable treatment time $T_{max}$, a patient blood conductivity or concentration target $Cp_{end}$, the urea distribution volume $V_O$ for the patient.

As it will appear clear the controller 2 of this embodiment is programmed not only for achieving the aims of the controller programmed according to FIG. 4 steps, but also for controlling the conductivity or concentration of the treatment liquid entering the second compartment as a function of said blood conductivity or concentration target $Cp_{end}$.

Indeed, in accordance with the embodiment of FIG. 5, the controller executes the same identical steps 42, 43,44, 45, 46, 47, 48, 49, 50, 51,52 above described with reference to FIG. 4 and then, after step 51, is programmed for changing, if necessary, at each time interval, the conductivity or concentration of the treatment liquid entering the second compartment in order to have blood conductivity or concentration for a substance reaching said conductivity or concentration target $Cp_{end}$ on or before said estimated total treatment time $T_{tot}$ (step 53 in FIG. 5).

Notice that step 53 can equivalently be carried out before steps 50, 51, as soon as the controller has estimated a remaining treatment time or a total treatment time at time interval $T_i$.

The step 53 of modifying of treatment liquid conductivity or concentration Cd comprises the following sub-steps:
i. Determining a calculated value $C_{di}$ of the conductivity or concentration for a substance $C_d$ as a function of the interval target $C_{pi}$ and of the measured instantaneous dialysance or clearance $D_i$ or $K_i$ for time Ti,
ii. Bringing the conductivity or concentration for a substance $C_d$ of treatment liquid entering the second compartment to said calculated value $C_{di}$ In detail the determining step uses one of the following formulas wherein $V_0$ represents the urea distribution volume for the patient:

$$C_d = C_{di} = \frac{C_{P_i} - C_{P_{i-1}} e^{-\frac{D_i}{V_0}(T_i - T_{i-1})}}{1 - e^{-\frac{D_i}{V_0}(T_i - T_{i-1})}} \qquad C_d = C_{di} = \frac{C_{P_i} - C_{P_{i-1}} e^{-\frac{K_i}{V_0}(T_i - T_{i-1})}}{1 - e^{-\frac{K_i}{V_0}(T_i - T_{i-1})}}$$

In the above formulas the interval target blood conductivity or concentration $Cp_i$ for the patient's blood relating to a time interval $t_i$, according to the following steps:
evaluating if the elapsed treatment time Ti is more or less of a prescribed value Tp,
assigning as interval target blood $Cpi=Cp_{end}+A$, wherein A is a positive value, if Ti less than Tp
assigning as interval target blood $Cpi=Cp_{end}$, if Ti more than or equal to Tp.

In the embodiment shown, the prescribed value Tp is less than Ttot an equal to $T_{tot}$ reduced by one hour.

After the detailed description concerning the embodiments of FIGS. 2, 3, 4 and 5, here below are disclosed further features of the invention which can be employed in any of the embodiments wherein an estimated total treatment time or an estimated remaining treatment time are being calculated in use by the controller 2.

Figure 6:
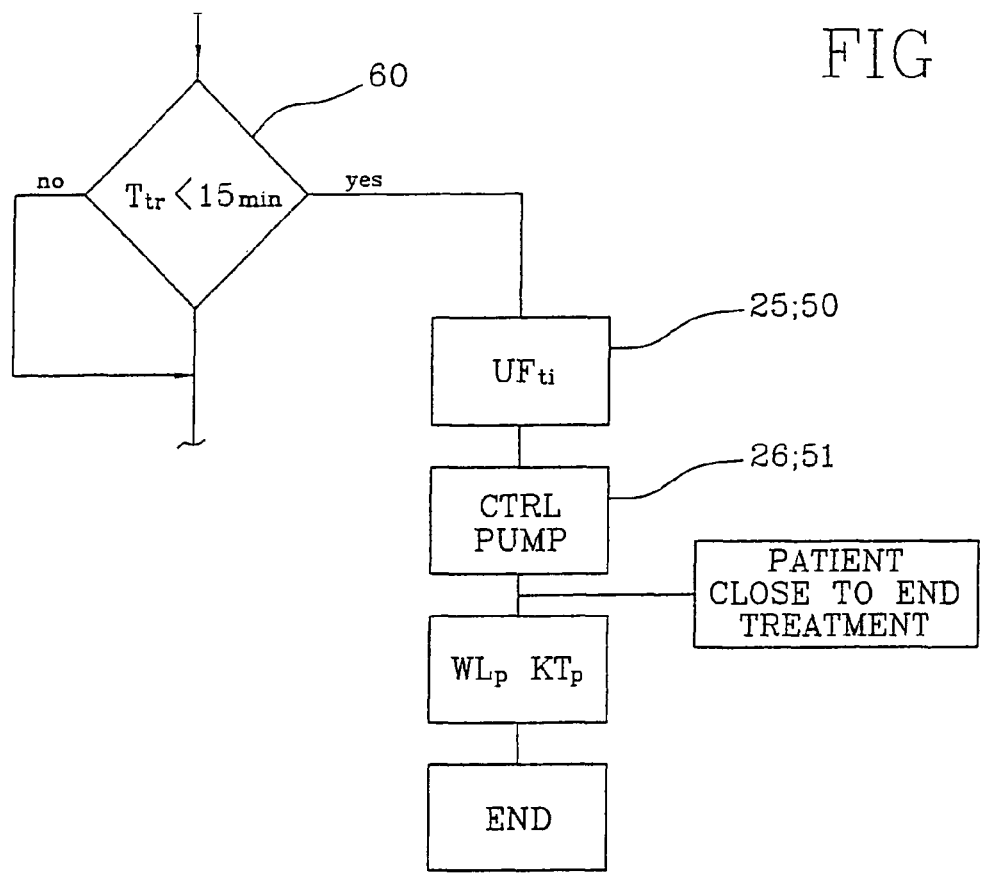
FIGS. 6 and 7 are flow diagrams of routines, which can be executed by the controller of the invention as part of its working principle.

In detail, as shown in FIG. 6, the controller is programmed to carry out an end treatment test 60 to check if the remaining treatment time $T_{tr}$ is less than a prescribed value, for instance 15 minutes. In the negative the cycle continues with no changes while in the affirmative the removal rate at time $T_i$ is calculated and set for the last time (blocks 25, 26; 50, 51) and an output signal is sent to an output device, such as display unit 19.

Figure 7:
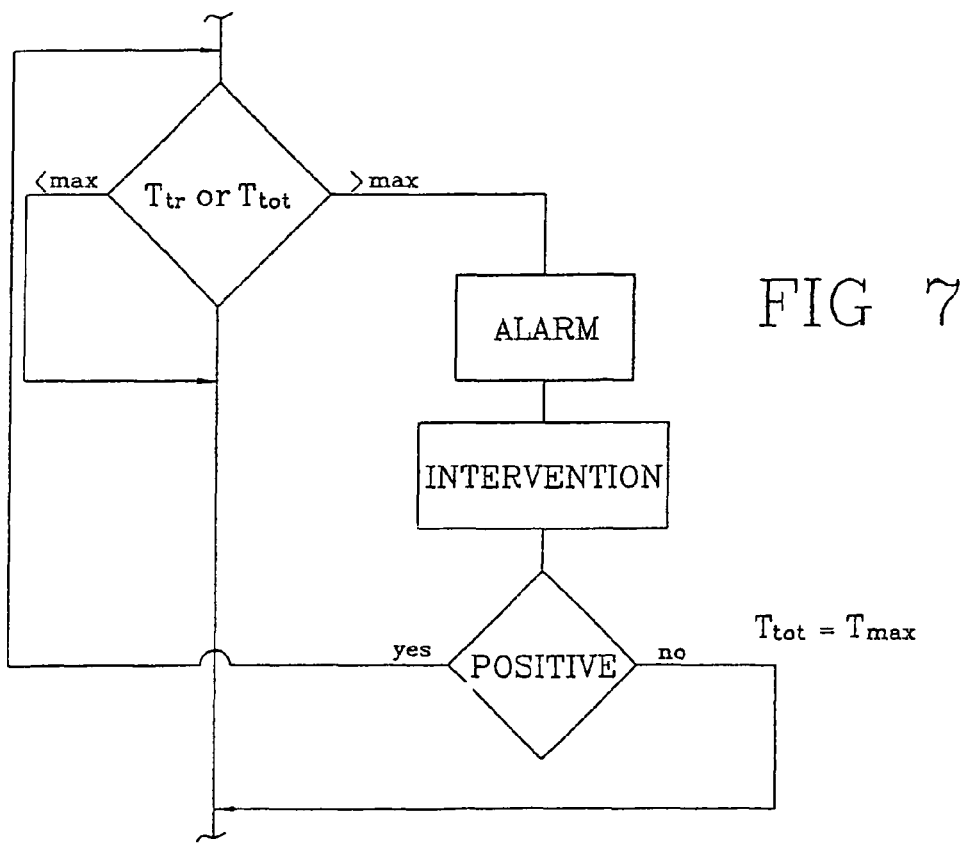

In FIG. 7 an alarm procedure is shown, which could be activated in case the estimated treatment time is greater than the maximum acceptable treatment time. Indeed as shown in FIG. 4 the controller could either assign as total treatment time the maximum treatment time and then warn the operator that the prescribed dialysis dose will not be fulfilled or put the machine in bypass mode and ask for intervention of an operator. Notice that in some circumstances the presence of bubbles in the dialysis line or other factors degrade the performances of the treatment unit, which can recover however its normal properties upon appropriate corrections are carried out. If the operator action is positive then the calculation of the estimated remaining or total treatment time is repeated. If again the problem persists no further intervention is requested, the machine is put in permanent bypass mode (lines 11 and 12 connected bypassing second compartment 5) and an alarm given.

Please also notice that in the embodiments shown the controller is programmed to generate a control signal (arrow 's' in FIG. 1) to automatically control the fluid removal rate from said second compartment by controlling the variable speed ultrafiltration pump 13. However the fluid removal rate from the second compartment could be controlled in a different way depending upon the hydraulic structure and configuration of the dialysis circuit.

The controller is also associated to display unit 19 which can operate as alert device, and which can be activated if the expected treatment procedure time or remaining hemodialysis treatment time are not within a prefixed range.

The display 19 is also adapted to display at the time intervals $T_i$ one or more of the values of the group comprising:
remaining time $T_{tr}$,
total treatment time $T_{tot}$,
clearance of dialysance measurements at the elapsed time $T_i$,
achieved dialysis dosage $KT_{Ti}$ after $T_i$ time,
achieved weight loss $WL_{Ti}$ after $T_i$ time,
achieved patient's conductivity after $T_i$ time,
prescribed value for more of the significant parameters,
a value proportional to one or more of the above values.

Figure 8:
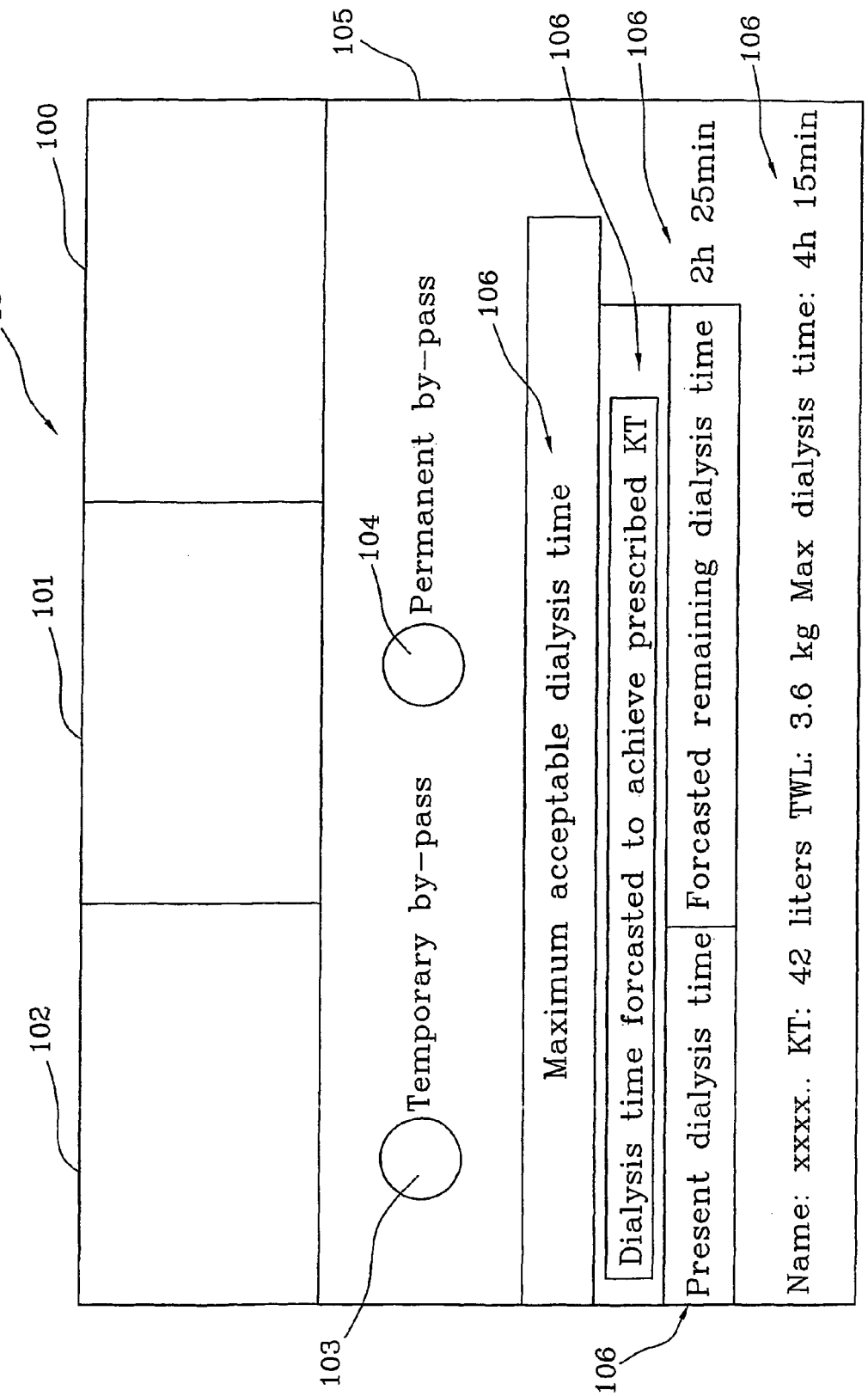
FIG. 8 schematically shows a display screen that would be associated with the controller and equipment of the invention.

In FIG. 8 an embodiment of a display unit 19 is shown. The display unit comprises three fields 100, 101, 102 each of a respective colour which are controlled by controller 2 to flash when specific events occur. First field can be for instance green and flashes when the prescribed value for one or more relevant parameter is or are reached. The second field can be for instance orange and controlled to flash when the patient is close to the treatment end (block 61).

The third field, for instance red, can be controlled to flash in case of an alarm condition, for instance when the prescribed value $KT_p$ cannot be reached within a maximum acceptable treatment time (block 52).

The display unit can also comprise an area 105 including pictograms 103, 104 which can be activated to signal the two bypass modes above described, and various additional fields for displaying alphanumerical strings 106 relating to the above prescribed and achieved significant parameters.

In addition to what already described it is also convenient to shortly underline some further possible variants to the above-described embodiments. As already mentioned, the total treatment time $T_{tot}$ or remaining treatment time $T_{tr}$ at time $T_i$ is regularly recalculated and updated at regular, for instance identical, time intervals during treatment, on the basis of the last or most recent instantaneous measured clearance or dialysance value $D_{Ti}$. As an alternative the remaining treatment time and therefore also the fluid removal rate from the second compartment at time Ti can be calculated as known functions of more then one measured clearance or dialysance values. Thus, any such changes in parameters which take place during a hemodialysis treatment procedure which may influence the dialysance or clearance of a hemodialyser product, such as blood flow rate, dialysis fluid flow rate, alterations in the permeability of the semi-permeable membrane of the hemodialyser product, will automatically be accounted for each time the treatment time is recalculated. This procedure of the invention accordingly provides a reliable means for securing a measure of the treatment time required to secure the prescribed dialysis dosage value $KT_p$.

It should also be borne in mind that it is one objective of the present invention to secure control over the actual total dialysis dosage delivered to a patient; this control can for example be achieved, in accordance with the invention, by computing a hemodialysis treatment procedure time as a function of calculated values related to one or more of the above identified significant parameters (such as an effective clearance or dialysis dosage value reached after at treatment time Ti); a basic component of such computation would comprise a determination of a treatment time as a function of such one or more calculated values. Thus, in this example, a computed total effective treatment time would need to be a function of one or more values $KT_{t1}, KT_{t2}, KT_{t3}, ---, KT_{tn}$, calculated in vivo using any known method after determined time increments $\Delta t$=say 5 min. For practical reasons it may only be possible to obtain a first measured value after about say 15 min of effective treatment time. Presuming this to be the case, a reasonably accurate assessment of an initial clearance or dosage value $KT_{ti}$, which has been achieved during said 15 min initial treatment time can be obtained by assuming that the measured clearance value or dosage delivered, for example after a 5 min interval, will substantially equate with the clearance value delivered over the same time period before the first measurement is made. Successive measurements of clearance values would generally be at least fractionally different from one another in that these values are dependent on changes (usually lowering) of the clearance capacity of the dialyser product during a treatment procedure, changes of blood rate, possible recirculation of treated blood, presence of bubbles in the dialysis liquid, dialysis liquid flow rate, ultrafiltration rate and other changes.

Also notice that measurements of clearance values would only be made during effective treatment times, i.e. while blood and dialysis liquid are flowing through the hemodialyser product. The controller is accordingly programmed to initiate measurements only during effective treatment times and similarly only compute or integrate effective treatment times to arrive at a computed hemodialysis treatment procedure time during effective treatment times.

It would be possible to compute a hemodialysis treatment procedure time as a function of measured values in various fashions, e.g. by reference of the difference between successive total dialysis dosage values to a reference difference value and to compute an increase or decrease in the treatment time proportional to deviations from the reference difference value. Such a procedure could for example be realised more readily if a standardised total clearance or dialysis dosage value is to be achieved.

Finally, it is to be noted that the invention relates also to program storage means including a program for the programmable controller 2; the program when executed by the controller programs the controller to perform the steps disclosed above and shown in the attached drawings. The program storage may comprise an optical data carrier and/or a magnetic data carrier and or a volatile memory support, which can be read or associated or put into communication with the controller for programming this latter.

The invention claimed is:

1. A controller for a blood treatment equipment, said equipment comprising at least a treatment unit including a semipermeable membrane separating the treatment unit in a first compartment for the circulation of blood and in a second compartment for the circulation of a treatment liquid, the controller being configured to:
receive one or more entries of measured information measured during the course of a treatment procedure, determine at time intervals during treatment:
a parameter selected from the group consisting of an instantaneous clearance $K_{Ti}$ measured at an elapsed treatment time $T_i$ and a dialysance value $D_{Ti}$ measured at an elapsed treatment time $T_i$; and
an effective total dialysis dosage $K^*T_{Ti}$ value which has been delivered at the elapsed treatment time $T_i$, wherein the controller is also configured to compare said calculated dialysis dose $K^*T_{Ti}$ to at least a total dialysis dosage value $K^*T_p$ to be achieved at the end of the treatment and to generate at least one output control signal responsive to said comparison for automatically controlling one or more operations performed by the equipment, the controller also being configured to determine at least one timing selected from the group consisting of an estimated remaining treatment procedure time $T_{tr}$ and an estimated total treatment time $T_{tot}$ required for achieving said prescribed total dialysis dosage value $KT_p$.

2. A controller according to claim 1, wherein the controller generates the output control signal responsive to said comparison for automatically controlling a fluid removal rate from said second compartment.

3. A controller according to claim 1, wherein said controller is programmed for determining the estimated remaining treatment procedure time $T_{tr}$ as a function of said total dialysis dosage value $KT_p$, the effective total dialysis dosage $KT_{ti}$ achieved by time $T_i$, and of the instantaneous clearance $K_{Ti}$; or dialysance value $D_{Ti}$ measured at treatment time $T_i$.

4. A controller according to claim 1, wherein said controller is programmed for determining the estimated total treatment time $T_{tot}$ as a function of said total dialysis dosage value $KT_p$, of the effective total dialysis dosage $KT_i$ achieved by time $T_i$, and of the elapsed treatment time $T_i$.

5. A controller according to claim 3, wherein said controller, at each time interval, is programmed for updating the estimated total treatment time $T_{tot}$ as sum of the elapsed treatment time $T_t$ and of the estimated value of the remaining treatment procedure time $T_{tr}$.

6. A controller according to claim 3 or 4, wherein said prescribed parameter also comprises a prescribed total weight loss $WL_p$ to be achieved at the end of the treatment, said controller being programmed for performing the following further steps at time intervals during treatment:
determining of an actual measured total weight loss $WL_{Ti}$ achieved by time $T_i$, and
setting of fluid removal rate UF from said second compartment for achieving a prescribed total weight loss $WL_p$ substantially at the same time as the prescribed total dialysis dosage value $KT_p$ is achieved.

7. A controller according to claim 6, wherein the controller is programmed for controlling, on an ongoing basis, the fluid removal rate as a function of the estimated remaining treatment procedure time $T_{tr}$ or of estimated total treatment time $T_{tot}$.

8. A controller according to claim 7, wherein said controlling comprises setting of the fluid removal rate $UF_{Ti}$ at time $T_i$ equal to the prescribed total weight loss $WL_p$ less the measured weight loss $WLT_i$ at time $T_i$, divided by the estimated remaining treatment time $T_{tr}$, according to the formula:

$$UF_{Ti} = \frac{WL_p - WL_{Ti}}{T_{tr}}.$$

9. A controller according to claim 7, wherein said controlling step comprises setting of the fluid removal rate $UFT_i$ at time $T_i$ equal to the prescribed total weight loss $WL_p$ less the measured weight loss $WL_{Ti}$ at time $T_i$, divided by a difference between the estimated total treatment time $T_{tot}$ and the elapsed treatment time $T_t$ according to the formula:

$$UF_{Ti} = \frac{WL_p - WL_{Ti}}{T_{tot} - T_i}.$$

10. A controller according to claim 1, wherein the controller is programmed for recalculating and updating at regular time intervals during treatment the estimated total treatment time $T_{tot}$ and/or the estimated remaining treatment time $T_{tr}$, on the basis of the most recent value or values of instantaneous clearance $K_{Ti}$ or dialysance $D_{Ti}$.

11. A controller according to claim 1, wherein the controller is programmed for recalculating and updating at regular time intervals during treatment the effective total dialysis dosage $KT_{Ti}$, value, which has been delivered at the elapsed effective treatment time $T_i$.

12. A controller according to claim 1, wherein the instantaneous clearance value $K_{Ti}$ or instantaneous dialysance value $D_{Ti}$ is determined at treatment time $T_i$, by a method comprising the following sub-steps:
  sending at least a first liquid through the second compartment of the treatment unit,
  sending at least a second liquid through the second compartment of the treatment unit, the second liquid having conductivity or concentration for at least a solute different from that of the first liquid,
  measuring the conductivity or concentration values of said substance in the treatment liquid downstream the treatment unit at least for both said first and for said second liquid, and
  calculating the instantaneous clearance $KT_i$ or instantaneous dialysance value $D_{Ti}$ at least as a function of said measured conductivity or concentration values.

13. A controller according to claim 1, wherein the effective total dialysis dosage $KT_{Ti}$ value, which has been delivered at the determined effective treatment time $T_i$, is calculated as an integration over time of effective instantaneous clearance $K_{Ti}$ or instantaneous dialysance $D_{Ti}$ values determined at the various regular time intervals $T_i$.

14. A controller according to claim 1, wherein the effective total dialysis dosage $KT_i$ value, which has been delivered at the effective treatment time $T_i$ is calculated as the product of the treatment time $T_i$ by a mean value of effective instantaneous clearance $K_{Ti}$ or of instantaneous dialysance $D_{Ti}$ values determined at the various regular time intervals $T_i$.

15. A controller according to claim 1, wherein said controller, at each time interval, is programmed for:
  calculating a sum of the elapsed treatment time $T_i$ with the calculated value of the remaining treatment procedure time $T_{tr}$,
  comparing said sum with a minimum treatment time $T_{min}$ and with a maximum treatment time $T_{max}$,
  setting a total treatment time $T_{tot}$ equal to the minimum treatment time $T_{max}$, if said sum is less then the minimum treatment time $T_{min}$,
  setting a total treatment time $T_{tot}$ equal to the maximum treatment time $T_{max}$, if said sum is more then the minimum treatment time $T_{max}$,
  setting a total treatment time $T_{tot}$ equal to said sum if the sum is neither less then the minimum treatment time $T_{min}$ nor more then the minimum treatment time $T_{max}$.

16. A controller according to claim 15, wherein said prescribed parameter also comprises a prescribed total weight loss $WL_p$ to be achieved at the end of the treatment, said controller being programmed for performing the following further steps at time intervals during treatment:

determining of an actual measured total weight loss $WL_{Ti}$ achieved by time $T_i$, and
setting of fluid removal rate from said second compartment for achieving a prescribed total weight loss $WL_p$ at said total treatment time $T_{tot}$.

17. A controller according to claim 16, wherein the controller is programmed for controlling, on an ongoing basis, the fluid removal rate $UF_{Ti}$ at time $T_i$ as a function of the total treatment time $T_{tot}$ by setting the $UF_{Ti}$ fluid removal rate at time $T_i$ equal to the prescribed total weight loss $WL_p$ less the measured weight loss $WL_{Ti}$ at time $T_i$, divided by the difference between the calculated total treatment time $T_{tot}$ and the elapsed treatment time $T_i$ according to the formula:

$$UF_{Ti} = \frac{WL_p - WL_{Ti}}{T_{tot} - T_i}.$$

18. A controller according to claim 16, wherein the controller is programmed for recalculating and updating the total treatment time $T_{tot}$ and/or the remaining treatment time $T_{tr}$ at regular time intervals during treatment, on the basis of the last or most recent instantaneous measured value or values of clearance $K_{Ti}$ or dialysance $D_{Ti}$.

19. A controller according to claim 16, wherein the controller is programmed for recalculating and updating at regular time intervals during treatment the effective total dialysis dosage $KT_{Ti}$ value which has been delivered at the elapsed effective treatment time $T_i$.

20. A controller according to claim 16, wherein the effective total dialysis dosage $K_{Ti}$ value, which has been delivered at the determined effective treatment time $T_i$, is calculated as an integration over time of effective instantaneous dialysis dosage values $DT_i$ determined at the various regular time intervals $T_i$.

21. A controller according to claim 1, wherein the prescribed reference value comprises a patient blood conductivity or concentration target $Cp_{end}$ to be achieved, said controller being programmed for changing, if necessary, at each time interval, the conductivity or concentration of the treatment liquid entering the second compartment in order to have blood conductivity or concentration for a substance reaching said conductivity or concentration target $Cp_{end}$ on or before said estimated total treatment time $T_{tot}$.

22. A controller according to 6, wherein the prescribed reference value comprises a patient blood conductivity or concentration target $Cp_{end}$ to be achieved, said controller being programmed for changing, if necessary, at each time interval, the conductivity or concentration of the treatment liquid entering the second compartment in order to have blood conductivity or concentration for a substance reaching said conductivity or concentration target $Cp_{end}$ on or before said estimated total treatment time $T_{tot}$.

23. A controller according to claim 1, wherein the prescribed reference value comprises a patient blood conductivity or concentration target $Cp_{end}$ be achieved, said controller being programmed for performing the following steps at each time interval $t_i$ during at least a part of said treatment:
  determining an interval target blood conductivity or concentration $C_i$ for the patient's blood, relating to a elapsed time $T_i$, and
  modifying, if necessary, the conductivity or concentration for a substance $C_d$ of treatment liquid entering the second compartment to have the patient plasmatic conductivity reaching the interval target $Cp_i$.

24. A controller according to claim 23, wherein said modifying of treatment liquid conductivity or concentration $C_d$ comprises the following sub-steps:
   determining a calculated value $C_{di}$ of the conductivity or concentration for a substance $C_d$ as a function of the interval target $C_{pi}$ and of the measured instantaneous dialysance or clearance $D_i$ or $K_i$ for time $T_i$,
   bringing the conductivity or concentration for a substance $C_d$ of treatment liquid entering the second compartment to said calculated value $C_{di}$.

25. A controller according to claim 24, wherein the said determining step uses the following formula:

$$C_d = C_{di} = \frac{C_{Pi} - C_{P_{i-1}} e^{-\frac{Di}{V_0}(T_i - T_{i-1})}}{1 - e^{-\frac{Di}{V_0}(T_i - T_{i-1})}}$$

wherein $V_0$ represents the urea distribution volume for the patient.

26. A controller according to claim 24, wherein the said determining step uses the following formula:

$$C_d = C_{di} = \frac{C_{Pi} - C_{Pi-1} e^{-\frac{Ki}{V_0}(Ti - Ti-1)}}{1 - e^{-\frac{Ki}{V_0}(Ti - Ti-1)}}$$

wherein $V_0$ represents the urea distribution volume for the patient.

27. A controller according to claim 23, wherein the controller is programmed for calculating said interval target blood conductivity or concentration $Cp_i$ for the patient's blood relating to a time interval $T_i$, according to the following steps:
   evaluating if the elapsed treatment time $T_i$ is more or less of a prescribed value $T_p$,
   assigning as interval target blood $Cp_i = Cp_{end} + A$, wherein A is a positive value, if $T_i$ less than $T_p$, and
   assigning as interval target blood $Cp_{i=Cpend}$, if $T_i$ more than or equal to $T_p$.

28. A controller according to claim 27, wherein the prescribed value $T_p$ is less than $T_{tot}$.

29. A controller according to claim 28, wherein the prescribed value $T_p$ is equal to $T_{tot}$ reduced by one hour.

30. Blood treatment equipment comprising at least a treatment unit including a semipermeable membrane separating the treatment unit in a first compartment for the circulation of blood and in a second compartment for the circulation of a treatment liquid, and a controller according to claim 1.

31. Equipment according to claim 30, comprising measuring means connected to the controller for measuring at least one of:
   conductivity of the of the treatment liquid downstream the treatment unit; or
   concentration of a substance in the treatment liquid downstream the treatment unit.

32. Equipment according to claim 30, comprising measuring means for measuring at least one of:
   conductivity of the of the treatment liquid upstream the treatment unit; or
   concentration of a substance in the treatment liquid upstream the treatment unit.

33. Equipment according to claim 31, comprising measuring means for measuring comprises a conductivity cell or an ion selective sensor or a urea sensor, operating on a conduit downstream the treatment unit.

34. Equipment according to claim 32, comprising measuring means for measuring comprises a conductivity cell or an ion selective sensor, operating on a conduit upstream the treatment unit.

35. Equipment according to claim 30 also including entry means for entering prescribed reference value or values for the significant parameter or parameters.

36. Equipment according to claim 30, comprising a variable speed ultrafiltration pump, in which the controller is programmed to generate a control signal to automatically control the fluid removal rate from said second compartment by controlling the variable speed ultrafiltration pump.

37. Equipment according to claim 30, wherein the controller is associated with an alert device, and the controller is programmed to activate said alert device if the expected treatment procedure time or remaining hemodialysis treatment time are not within a prefixed range.

38. Equipment according to claim 30, in which the controller is associated with a display screen adapted to display at the time intervals $T_i$ one or more of the values selected from the group consisting of:
   remaining time $T_{tr}$,
   total treatment time $T_{tot}$,
   clearance of dialysance measurements at the elapsed time $T_i$,
   achieved dialysis dosage $KT_{Ti}$ after $T_i$ time,
   achieved weight loss $WL_{Ti}$ after $T_i$ time,
   achieved patient's conductivity after $T_i$ time,
   prescribed value for more of the significant parameters, and
   a value proportional to one or more of the above values.

39. A controller for a blood treatment equipment, said equipment comprising at least a treatment unit including a semipermeable membrane separating the treatment unit in a first compartment for the circulation of blood and in a second compartment for the circulation of a treatment liquid, the controller being configured to:
   receive a reference value of a first prescribed parameter consisting of the total clearance value $K_{Tp}$ to be achieved at the end of the treatment,
   receive a reference value of a second prescribed parameter consisting of a prescribed total weight loss $WL_p$ to be achieved at the end of the treatment,
   determine a prescribed rate R by dividing said total weight loss $W_{Lp}$ to be achieved at the end of the treatment by said total dialysis dose value $K_{Tp}$ to be achieved at the end of the treatment,
   determine at time intervals during treatment:
      a parameter selected from the group consisting of an instantaneous clearance $K_T$ measured at an elapsed treatment time $T_i$ and a dialysance value $D_{Ti}$ measured at an elapsed treatment time $T_i$; and
   control the rate of fluid removal from the second compartment of the blood treatment, said controlling comprising keeping said rate of fluid removal $UF_{Ti}$ at time $T_i$ substantially equal to the product of said prescribed rate R by the instantaneous clearance $K_{Ti}$ or instantaneous dialysance value $D_{Ti}$ measured at treatment time Ti.

* * * * *

UNITED STATES PATENT AND TRADEMARK OFFICE
CERTIFICATE OF CORRECTION

PATENT NO. : 8,512,564 B2  Page 1 of 1
APPLICATION NO. : 10/526498
DATED : August 20, 2013
INVENTOR(S) : Bene et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2516 days.

Signed and Sealed this

Fifteenth Day of September, 2015

Michelle K. Lee
*Director of the United States Patent and Trademark Office*